United States Patent [19]

Leighton et al.

[11] Patent Number: 5,187,006

[45] Date of Patent: Feb. 16, 1993

[54] N-ALLYL-N-DIALKOXYETHYL AMIDE OR AMINE EMULSION BINDERS FOR NONWOVEN FABRICS

[75] Inventors: John C. Leighton, Flanders, N.J.; Dennis Neigel, Salisbury, N.C.; Carmine P. Iovine, Bridgewater, N.J.

[73] Assignee: National Starch and Chemical Investment Holding Corporation, Wilmington, Del.

[21] Appl. No.: 930,871

[22] Filed: Aug. 14, 1992

Related U.S. Application Data

[62] Division of Ser. No. 764,745, Sep. 24, 1991.

[51] Int. Cl.$^5$ .............................. D04H 1/64
[52] U.S. Cl. ................... 428/288; 428/290; 526/304; 427/385.5; 427/389; 427/389.9; 427/393.5; 524/812
[58] Field of Search ............ 428/288, 290; 427/389, 427/393.5; 524/812; 526/304

[56] References Cited

U.S. PATENT DOCUMENTS

| | | | |
|---|---|---|---|
| 4,110,101 | 8/1978 | Stach et al. | 71/88 |
| 4,647,611 | 3/1987 | Goldstein et al. | 524/458 |
| 4,788,288 | 11/1988 | Pinschmidt, Jr. et al. | 544/212 |
| 4,959,489 | 9/1990 | Nordquist et al. | 560/170 |

Primary Examiner—Joseph L. Schofer
Assistant Examiner—M. Nagumo
Attorney, Agent, or Firm—Jane E. Gennaro; Edwin M. Szala

[57] ABSTRACT

A formaldehyde-free latent crosslinking monomer represented by the formula

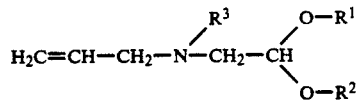

in which $R^1$ and $R^2$ are $C_1$-$C_3$ alkyl; $R^3$ is hydrogen, $C_1$-$C_3$ alkyl, or $R^4$—C(O)—; and $R^4$ is $C_1$-$C_3$ alkyl or $C_6$-$C_8$ aryl, contains an allyl group capable of undergoing addition copolymerization and a dialkoxy ethyl group capable of crosslinking under acidic conditions. The monomer can be copolymerized with comonomers to form emulsion polymers for use as formaldehyde-free binders in nonwoven textiles. Methods for the preparation of the monomer, the polymers, and the nonwoven fabrics are described.

9 Claims, No Drawings

N-ALLYL-N-DIALKOXYETHYL AMIDE OR AMINE EMULSION BINDERS FOR NONWOVEN FABRICS

This application is a division of application Ser. No. 07/764,745 filed Sep. 24, 1991, now allowed.

FIELD OF THE INVENTION

This invention is directed to N-allyl-N-dialkoxyethyl amide or amine monomers, their preparation, and their use as crosslinking agents in emulsion copolymers that can be thermoset without the release of formaldehyde. This invention is further directed to nonwoven fabrics bonded with those emulsion copolymers and a process for the preparation of those nonwoven fabrics.

BACKGROUND OF THE INVENTION

Emulsion polymers are widely used to bind nonwoven fibers into fabrics for use as facings or topsheets in diapers, bed pads, hospital gowns, and other such uses. The typical emulsion polymers for this use are prepared predominantly from ehtylene, vinyl acetate, vinyl chloride and acrylate esters in combination with styrene or acrylonitrile, and use N-methylolacrylamide as the cross-linking agent. Although N-methylolacrylamide is widely used in the industry and provides excellent wet and dry tensile strength to the nonwoven fabrics, it suffers from two major drawbacks. N-methylolacrylamide is an equilibrium composition of acrylamide with free formaldehyde. Formaldehyde is a suspected carcinogen. A latex that uses N-methylolacrylamide as a latent crosslinking monomer will contain quantities of free formaldehyde, and consequently the nonwoven substrates bound with emulsion polymers containing N-methylolacrylamide will contain detectable quantities of free formaldehyde. In addition, acrylamide derivatives, including N-methylol acrylamide, are capable of undergoing strongly exothermic homopolymerization reactions, which makes processing, transportation and storage of acrylamides difficult.

The N-allyl-N-dialkoxyethyl amide or amine monomer of the present invention is not in equilibrium with free formaldehyde, yet it provides latent crosslinking ability similar to the N-methylolacrylamide compounds. It also does not undergo strongly exothermic homopolymerization reactions.

U.S. Pat. No. 4,788,288, issued to Pinschmidt, Jr. et al., discloses N-olefinically substituted cyclic hemiamidals and hemiamide ketals, and N-olefinically substituted dialkyl acetals and ketals, which can be incorporated into free radical addition polymers to give formaldehyde-free compositions. U.S. Pat. No. 4,959,489 issued to Nordquist et al. discloses a process for making an N-substituted acrylamide containing dialkyl acetal groups. However, the starting materials for some of these compositions are expensive and there is still a need for inexpensive formaldehyde-free compositions for use in emulsion binders for nonwoven fabrics.

SUMMARY OF THE INVENTION

This invention provides formaldehyde-free monomers, emulsion copolymers formed with those monomers, and nonwoven fabrics bound by the emulsion copolymers. This invention also provides a process for the preparation of the monomer and a process for the preparation of the nonwoven fabric. The monomer is an N-allyl-N-dialkoxyethyl amine or amide, given the acronym NANDA, which can be copolymerized with one or more monoethylenically unsaturated comonomers to provide an emulsion binder for nonwoven fabrics. The fabrics bound with a binder formed from the NANDA monomer have comparable dry strength and solvent strength to fabrics formed with binder cross-linked with the N-methylolacrylamide, NMA.

DETAILED DESCRIPTION OF THE INVENTION

The N-allyl-N-dialkoxyethyl amide or amine monomers of the invention are represented by the formula:

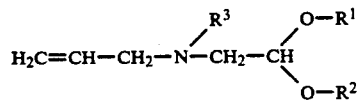

in which $R^1$ and $R^2$ are $C_1$-$C_3$ alkyl; $R^3$ is hydrogen, $C_1$-$C_3$ alkyl, or $R^4$—C(O)—; and $R^4$ is $C_1$-$C_3$ alkyl or $C_6$-$C_8$ aryl. Preferably, $R^1$ and $R^2$ are independently methyl or ethyl and $R^3$ is $CH_3$—C(O)—.

The monomer compounds of the invention are easily prepared through two routes utilizing readily available and inexpensive starting materials. In one route, an amino acetaldehyde acetal is reacted with allyl chloride under basic conditions to give an N-allyl-N-dialkoxyethyl amine, which is optionally further reacted with an acylating agent to give an N-allyl-N-dialkoxyethyl amide. Alternatively, a chloroacetaldehyde acetal is reacted under mildly basic conditions with an allyl amine to give an N-allyl-N-dialkoxyethyl amine, which is optionally further reacted with an acylating agent to give an N-allyl-N-dialkoxyethyl amide.

The acetals used as starting materials can be prepared by standard organic synthesis methods. For example, U.S. Pat. Nos. 4,642,389 and 4,642,390 issued to Neigel disclose methods of manufacture of acetals suitable for starting materials.

The reactions for the synthesis of the amine and amide monomers can be carried out neat or in any solvent suitable to the reactant compounds and product. If solvents are used, solvents suitable for the amine synthesis are polar solvents, preferably water or isopropanol, and solvents suitable for the amide synthesis are nonpolar solvents, preferably diethyl ether or toluene.

The resulting monomers are liquids stable at room temperature or at moderately elevated temperatures (<50° C.) without the need for the addition of inhibitors to prevent homopolymerization.

In another embodiment, the N-allyl-N-dialkoxyethyl amines or amides can be copolymerized with other monomers to form emulsion polymers suitable for use as binders, particularly binders for making nonwoven fabrics. Suitable comonomers for copolymerization with the NANDA monomers include vinyl acetate, acrylic acid, acrylamide, olefins (such as ethylene), vinyl halides (such as vinyl chloride), $C_1$-$C_8$ alkyl acrylates or methacrylates, and mixtures of these comonomers.

The NANDA monomers are present in the copolymer in an amount from about 1% to about 10% by weight of the copolymer, and preferably from about 4% to about 6% by weight of the copolymer. The other copolymerizable monomers are present in the copolymer in an amount from about 90% to about 99% by weight of the copolymer, and preferably from about 94% to about 96% by weight of the copolymer.

Suitable monomer mixtures for copolymerization with the N-allyl-N-dialkoxyethyl amines or amides are a mixture of 50%–90% vinyl acetate and 50%–10% ethylene by weight of the comonomer mixture, mixtures of 50%–90% vinyl acetate and 50%–10% acrylate esters by weight of the comonomer mixture, or mixtures solely of acrylate and methacrylate esters.

The copolymer may also contain an hydroxyl-containing comonomer as a coreactant for the NANDA monomer. The coreactant monomer may be present in an amount up to about 10% by weight of the comonomer mixture. The preferred hydroxyl-containing reactive comonomers are hydroxyethyl acrylate or hydroxypropyl acrylate and the corresponding methacrylates.

The polymerization of the NANDA monomers with the above mentioned comonomers is effected by conventional batch, semi-batch or continuous emulsion polymerization techniques well known in the art. Generally, the comonomers are polymerized in an aqueous medium (under pressures not exceeding 100 atmospheres if ethylene is employed) in the presence of an initiator and at least one emulsifying agent.

The polymerization is initiated by an effective amount of a free-radical initiator such as hydrogen peroxide, ammonium persulfate, sodium persulfate, potassium persulfate, or tert-butyl hydroperoxide, in amounts of between 0.01% and 3% by weight, preferably 0.01% and 1% by weight based on the total amount of the emulsion. The free radical initiators can be used alone or in combination with suitable reducing agents, such as ferrous salts, sodium dithionite, sodium metabisulfite, sodium thiosulfate and ascorbic acid to form a resox initiator system employed in amounts of 0.01% to 3%, preferably 0.01% to 1% by weight of the total emulsion. The initiators can be charged in the aqueous emulsifier solution or be added during the polymerization in doses.

The polymerization is carried out at a pH of between 2 and 7, preferably between 3 and 5. In order to maintain the pH range, it may be useful to work in the presence of customary buffer systems, for example, in the presence of alkali metal acetates, alkali metal carbonates, or alkali metal phosphates. Polymerization regulators, like mercaptan, aldehydes, chloroform, ethylene chloride and trichloroethylene, can also be added when needed.

The emulsifying agents used in the polymerization can be any of those generally known and used in emulsion polymerizations. Suitable emulsifying agents are anionic, cationic or nonionic emulsifiers or surfactants, or mixtures of them. Examples of suitable anionic emulsifiers are alkyl sulfonates, alkylaryl sulfonates, alkyl sulfates, sulfates of hydroxyalkanols, alkyl and alkylaryl disulfonates, sulfonated fatty acids, sulfates and phosphates of polyethoxylated alkanols and alkylphenols, and esters of sulfosuccinic acid. Examples of suitable cationic emulsifiers are alkyl quaternary ammonium salts and alkyl quaternary phosphonium salts. Examples of suitable nonionic emulsifiers are the addition products of 5 to 50 moles of ethylene oxide adducted to straight-chain and branched-chain alkanols with 6 to 22 carbon atoms, or alkylphenols, or higher fatty acids, or higher fatty acid amides, or primary and secondary higher alkylamines, and block copolymers of propylene oxide with ethylene oxide. Combinations of these emulsifying agents may also be used, in which case it is advantageous to use a relatively hydrophobic emulsifying agent in combination with a relatively hydrophilic agent. The amount of emulsifying agent is generally from about 1% to 10%, preferably from about 2% to 8%, by weight of the monomers used in the polymerization.

Various protective colloids may also be used in place of, or in addition to, the emulsifiers described above. Suitable colloids include partially acetylated polyvinyl alcohol (e.g., up to 50% acetylated), casein, hydroxyethyl starch, carboxymethyl cellulose, gum arabic, and the like, as known in the art of synthetic emulsion polymer technology. In general, these colloids are used at levels of 0.5% to 4% by weight of the total emulsion.

The emulsifier or protective colloid used in the polymerization can be added in its entirety to the initial charge to the polymerization zone, or a portion of the emulsifier, for example, from 25% to 90%, can be added continuously or intermittently during polymerization. The particle size of the emulsion can be regulated by the quantity of nonionic or anionic emulsifying agent or protective colloid employed. To obtain smaller particle sizes, greater amounts of emulsifying agents are used. As a general rule, the greater the amount of the emulsifying agent employed, the smaller the average particle size.

The polymerization reaction is generally continued until the residual monomer content is below about 1% of total emulsion mass. The completed reaction product is then allowed to cool to about room temperature, while sealed from the atmosphere.

The emulsions are produced and used at relatively high solids contents, for example, between 35% and 70%, preferably not less than about 50%, although they may be diluted with water if desired.

When the emulsion polymers derived from the monomers of this invention are used as binders to prepare nonwoven fabrics, other additives conventionally employed in similar binders may be added to the emulsion. Examples of such additives are defoamers, pigments, catalysts, wetting agents, thickeners, and external plasticizers. The choice of additives and the amounts in which they are added are well known to those skilled in the art. These additives may be formulated into the emulsion binder if their stability in aqueous dispersion is high, or they may be added to the emulsion binder just before application if their stability in the emulsion is low.

Binders described above are suitably used to prepare nonwoven fabrics by a variety of methods known in the art. In another embodiment, this invention is directed to the nonwoven fabrics bonded with the emulsion polymers derived from the inventive monomers. In general, the nonwoven fabrics are formed from a loosely assembled web of fibers impregnated with the emulsion binder. Before the binder is applied to the web of fibers, it is mixed with a suitable catalyst to crosslink the emulsion binder to itself and to the fibers. After impregnation with the emulsion binder, the web of fibers is dried with heating, which serves to cure the binder. Suitable catalysts are known in the art, and can be, for example, hydrochloric acid, oxalic acid, citric acid, or salts such as ammonium chloride. The catalyst is generally present in an amount of about 0.5% to about 2% of the total polymer.

The starting fibrous web can be formed by any one of the conventional techniques, such as carding, garnetting, or air-laying, for depositing or arranging fibers in a web or mat. In general, the fibers extend in a plurality of diverse directions in general alignment with the major plane of the fabric, overlapping, intersecting and supporting one another to form an open, porous structure. Fibers that may be used in the starting web can be natural or synthetic fibers, such as natural and regenerated cellulose fibers (we define cellulose fibers to mean those that contain predominantly $C_6H_{10}O_5$ groupings), wool, cellulose acetate, polyamides, polyesters, acrylics, polyethylene, polyvinyl chloride, and polyurethanes, alone or in combination with one another.

The starting fibrous web preferably weighs from about 5 to about 65 grams per square yard and more preferably weighs from about 10 to about 40 grams per square yard. After formation, the starting fibrous web is subjected to one or more of the bonding operations used in the art to anchor the individual fibers together to form a self-sustaining web. The bonding operations widely used are overall impregnation, or imprinting the web with intermittent or continuous straight or wavy lines or areas of binder extending transversely or diagonally across the web, and if desired, also along the web.

The amount of binder, calculated on a dry basis, applied to the fibrous starting web ranges from about 10 to about 100 parts or more per 100 parts of the starting web, and preferably from about 20 to about 45 parts per 100 parts of the starting web.

After impregnation with binder, the web is dried, usually by passing it through an air oven or over sections of heated cans, and then cured, usually by passing it through a curing oven or over sections of hot cans. Ordinarily, convection air drying is effected at 65° to about 95° C. for 2-6 minutes, followed by curing at 145° to about 155° C. for 1-5 minutes. However, other time-temperature relationships can be employed, for example, shorter times at higher temperatures or longer times at lower temperatures, and these relationships are well known to one skilled in the art.

The following examples are given to illustrate the present invention, and are not to be construed to limit the scope and spirit of the invention.

EXAMPLES

Example 1

Preparation of N-allyl-N-dimethoxyethyl Acetamide

Aminoacetaldehyde dimethyl acetal was reacted with allyl chloride to give N-allyl-N-dimethoxyethyl amine, which was then acetylated with acetyl chloride to give N-allyl-N-dimethoxyethyl acetamide, according to the following reactions:

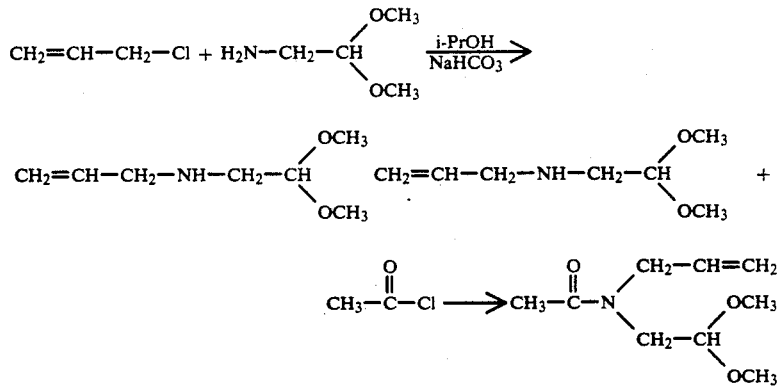

Aminoacetaldehyde dimethyl acetal (70.0 grams, 0.666 mole), allyl chloride (25.5 grams, 0.333 mole), and $NaHCO_3$ (42.0 grams, 2 moles), were added to 99% isopropanol (117.75 grams, approx. 115 ml) in a one liter pressure vessel, and heated approximately to 100° C. under 140 psi of pressure for six hours. The reaction mixture was cooled to room temperature and the contents filtered and washed with isopropanol under vacuum to remove the salt precipitate. The filtrate was concentrated on a rotary evaporator at 50° C. to remove the isopropanol and diluted with excess diethyl ether, 50–100 ml, to cause additional precipitation. The crystals were collected and the filtrate was again concentrated on a rotary evaporator at 50° C. to remove the ether and to give 43.5 grams of crude product. The crude product was distilled at reduced pressure and 16.8 grams of the product was isolated at 70°–72° C. The structure of the product, N-allyl-N-dimethoxyethyl amine, was confirmed by NMR.

N-allyl-N-dimethoxyethyl amine (16.0 grams, 0.11 mole) and triethylamine (11.1 grams) were added separately to the reaction flask with diethyl ether (100 ml, 70.7 grams), and cooled to about 5°–10° C. Acetyl chloride (8.7 grams, 0.11 mole) was added to the reaction flask over approximately 20 minutes while maintaining the temperature at less than 20° C. The reaction mixture was diluted with 150 ml of diethyl ether and held at room temperature for one hour. The reaction mixture was filtered to remove triethylamine hydrochloride. The solvent was removed by rotary evaporation to give 20.0 grams of liquid product, identified as N-allyl-N-dimethoxyethyl acetamide by NMR.

Example 2

Alternate Route: Preparation of N-allyl-N-dimethoxyethyl Acetamide

Chloroacetaldehyde dimethyl acetal was reacted with allyl amine to give N-allyl-N-dimethoxyethyl amine, which was then acetylated with acetyl chloride to give N-allyl-N-dimethoxyethyl acetamide according to the following reactions:

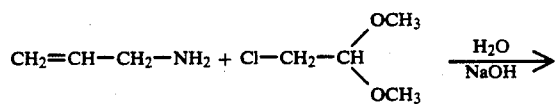

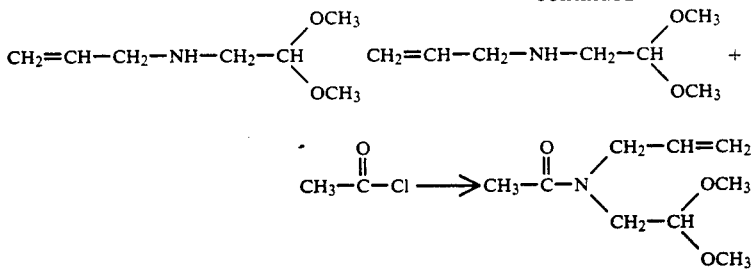

Allylamine (708 grams, 12.17 moles) and chloroacetaldehyde dimethylacetal (440 grams, 3.5 moles) were charged to a 2 liter stainless steel autoclave and heated with agitation to 130° C. for 6.5 hours at 40 psig pressure. The reaction was cooled and 25% aqueous sodium hydroxide (560 grams, 3.5 moles) was added. Analysis by gas chromatography indicated 99.4% of the starting chloroacetaldehyde dimethyl acetal had reacted with the allyl amine. Bis(dimethoxyethyl) allyl amine accounted for about 4% of the products formed. The sodium chloride precipitate was filtered out and the remaining reaction mixture was distilled at atmospheric pressure through a 12 inch Vigreaux column. A fraction (889 grams) distilled from 100° C. to 120° C. was isolated and analyzed by gas chromatography as 98.6% N-allyl-N-dimethoxyethyl amine in 30% aqueous solution.

N-allyl-N-dimethoxyethyl amine (30% aqueous, 48.3 grams, 0.10 mole) was added to a glass reaction vessel fitted with a mechanical agitator. The agitator was started and sodium hydroxide (4.44 grams, 0.11 mole) was dissolved in the aqueous amine. Toluene (50 grams) was added and the mixture cooled to 0° to 5° C. Acetyl chloride (8.24 grams, 0.105 mole) was added over 10 minutes while maintaining the temperature below 5° C. The reaction mixture was stirred for 30 minutes at 5° C., agitation was stopped, and the mixture allowed to phase separate. The aqueous layer was discarded. Toluene was removed from the organic layer by rotary evaporation and 14.8 grams (0.08 mole) of N-allyl-N-dimethoxyethyl acetamide was isolated as confirmed by NMR.

Examples 3-5

Preparation of Emulsion Copolymers

Example 3 is an emulsion copolymer prepared with vinyl acetate and N-methylolacrylamide, and represents the industry standard. Examples 4 and 5 are emulsion copolymers prepared with the amide form of the NANDA monomer of the instant invention. TABLE I shows the composition in grams of Examples 3, 4, and 5, in which Example 3 is copolymer A, Example 4 is copolymer B, and Example 5 is copolymer C.

A two-liter four-necked flask was equipped with a stainless steel stirrer, condenser, addition funnel, nitrogen inlet, thermometer, and hot water bath. Initial-charge 1 was charged to the flask and purged with nitrogen. Initial-charge 2 was added to the reactor and the contents were heated to 78°-80° C. Five minutes after polymerization initiation was observed, Slow-add 1 (the monomer pre-emulsion mixture) and Slow-add 2 were added uniformly to the reactor over a four hour period. When Slow-add 1 and Slow-add 2 were completely added, the polymerization mixture was held for 45 minutes at 78°-80° C. and then cooled to room temperature. The emulsion polymer was then discharged.

Examples 6-11

Preparation of Nonwoven Fibrous Webs

The three copolymer compositions of Examples 3, 4, and 5, were each used to impregnate nonwoven fibrous webs of an air-laid wood pulp and of rayon. The resulting six examples were composed as follows:

Example 6: Pulp fibers impregnated with copolymer A.

Example 7: Pulp fibers impregnated with copolymer B.

Example 8: Pulp fibers impregnated with copolymer C.

Example 9: Rayon fibers impregnated with copolymer A.

Example 10: Rayon fibers impregnated with copolymer B.

Example 11: Rayon fibers impregnated with copolymer C.

TABLE I

| Formula | Material | Ex. 3/A | Ex. 4/B | Ex. 5/C |
|---|---|---|---|---|
| Initial-Charge 1 | Distilled Water | 349.1 | 396 | 396 |
|  | Calsoft* 20% | 1.0 | 1.0 | 1.0 |
|  | Triton X305 70%** | 3.0 | 3.0 | 3.0 |
|  | Sodium Acetate | 0.6 | 0.6 | 0.6 |
|  | Ammonium Persulfate | 0.8 | 0.8 | 0.8 |
| Initial-Charge 2 | Vinyl Acetate | 50 | 50 | — |
|  | Butyl Acrylate | 5 | 5 | — |
|  | Ethyl Acrylate | — | — | 35 |
|  | Methyl Methacrylate | — | — | 20 |
| Slow-Add 1 | Distilled H$_2$O | 90 | 90 | 90 |
|  | Calsoft* 20% | 10 | 10 | 10 |
|  | Triton X305** 70% | 6 | 6 | 6 |
|  | Vinyl Acetate | 325 | 325 | — |
|  | Butyl Acrylate | 120 | 120 | — |
|  | Ethyl Acrylate | — | — | 332 |
|  | Methyl Methacrylate | — | — | 113 |
|  | N-Methylol Acrylamide 48% | 31.3 | — | — |
|  | NANDA*** 95% | — | 29.2 | 29.2 |
|  | Hydroxypropyl Acrylate | — | 19.3 | 19.3 |
| Slow-Add 2 | Distilled Water | 40 | 40 | 40 |
|  | Ammonium Persulfate | 1.0 | 1.0 | 1.0 |

*A surfactant sold by Pilot Chemical Company
**A surfactant sold by Union Carbide
***N-allyl-N-dimethoxyethyl acetamide The individual fibrous webs were immersed in a 15% solids emulsion bath of copolymer of A, B, or C, corresponding to the examples as defined above, for approximately one minute. After removal from the bath, the webs were passed through nip rolls to remove excess emulsion to give samples containing 10% binder for pulp and 25% binder for rayon based on the weight of the starting fiber. The webs were dried on a canvas covered drier, and then cured in a forced air oven for two minutes at a temperature of 300° F. The webs were cut into strips 5 inches (12.7 cm) in machine direction and 1 inch (2.54 cm) in cross machine direction and evaluated for percent absorption of the copolymer (% pick up in weight over the basis weight), and for peak load and percent elongation when dry, wet with water, and wet with methyl ethyl ketone (MEK). Peak load and percent elongation are measures of tensile strength as tested on an Instron tensile tester Model 1130 equipped with an environmental chamber at crosshead speed of 10 cm/min. The gauge length at the start of each test was 3 inches (7.62 cm). The results of the tests are shown in TABLE II.

TABLE II

| Example | 6 | 7 | 8 | 9 | 10 | 11 |
|---|---|---|---|---|---|---|
| Basis Weight* | 10.6 | 11.1 | 10.4 | 23.6 | 25.2 | 25.3 |
| % Pick Up | 36.8 | 37.3 | 37.3 | 21.4 | 18.4 | 17.9 |
| Dry Peak Load (lbs.) | 6.31 | 5.57 | 5.37 | 2.39 | 1.47 | 1.11 |
| Dry % Elong. | 5.8 | 6.1 | 6.1 | 11.1 | 10.8 | 11.3 |
| Wet Peak Load | 2.57 | 2.09 | 2.33 | 0.98 | 0.44 | 0.46 |
| Wet % Elong. | 10.2 | 10.4 | 10.1 | 25.8 | 28.9 | 27.7 |
| MEK** Peak Load | 1.61 | 1.78 | 2.17 | 0.61 | 0.19 | 0.21 |
| MEK % Elong. | 4.6 | 6.1 | 5.4 | 4.8 | 3.9 | 3.6 |

*in grams per square yard
**methyl ethyl ketone
Example 6 is pulp fiber impregnated with the industry standard emulsion polymer prepared with vinyl acetate and N-methylolacrylamide.
Example 7 is pulp fiber impregnated with an emulsion polymer prepared with NANDA and vinyl acetate.
Example 8 is pulp fiber impregnated with an emulsion polymer prepared with NANDA and acrylates.
Example 9 is rayon fiber impregnated with the industry standard emulsion polymer prepared with vinyl acetate and N-methylolacrylamide.
Example 10 is rayon fiber impregnated with an emulsion polymer prepared with NANDA and vinyl acetate.
Example 11 is rayon fiber impregnated with an emulsion polymer prepared with NANDA and acrylates.

The data in Table II show that the fibrous webs impregnated with the emulsion polymer formed from the NANDA monomer, which contains no formaldehyde, performed comparably on pulp and acceptably on rayon to the webs impregnated with the industry standard emulsion polymers formed with N-methylolacrylamide (NMA), which contain formaldehyde. Specifically, the NANDA containing emulsion polymers showed 85-88% of dry strength, 81-91% of wet strength, and 110-134% of solvent strength compared to the NMA containing lattices when used on air-laid wood pulp substrate, and 46-62% of dry strength, 45-47% of wet strength, and 31-34% of solvent strength compared to the NMA containing lattices when used on rayon substrate.

Various modifications and improvements on the above described examples will be apparent to those skilled in the art without departing from the spirit or scope of this invention.

We claim:

1. A nonwoven fabric formed from a loosely assembled web of fibers bonded together with a copolymer emulsion binder having a glass transition temperature of about −50° C. to about 50° C., comprising polymerized residues derived from
    (a) monomer units represented by the formula

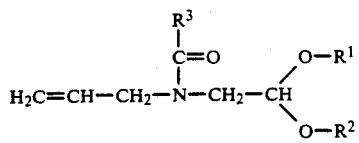

in which $R^1$ and $R^2$ are $C_1$-$C_3$ alkyl, and $R^3$ is $C_1$-$C_3$ alkyl or $C_6$-$C_8$ aryl, present in an amount of about 1 to about 10 parts by weight of total monomers;
    (b) comonomer units, copolymerizable with the monomer of (a), present in an amount of about 90 to about 99 parts by weight of total monomers;
    (c) optionally, hydroxyl-containing monomer units, coreactive with the monomer units of (a), present in an amount up to 10 parts by weight of total monomers.

2. The nonwoven fabric according to claim 1 bonded with the copolymer emulsion binder in which $R^1$ and $R^2$ of the monomer (a) are independently methyl or ethyl.

3. The nonwoven fabric according to claim 1 bonded with the copolymer emulsion binder in which the comonomer (b) is selected from the group consisting of acrylic acid, acrylamide, vinyl acetate, $C_2$-$C_6$ olefins, vinyl halides, $C_1$-$C_8$ alkyl acrylates or methacrylates, and mixtures of these comonomers.

4. The nonwoven fabric according to claim 3 bonded with the copolymer emulsion binder in which the comonomer (b) is a mixture of 50%-90% vinyl acetate and 50%-10% ethylene, by weight.

5. The nonwoven fabric according to claim 3 bonded with the copolymer emulsion binder in which the comonomer (b) is a mixture of 50%-90% vinyl acetate and 50%-10% $C_1$-$C_8$ acrylate esters by weight.

6. The nonwoven fabric according to claim 3 bonded with the copolymer emulsion binder in which the comonomer (b) is a mixture of acrylate and methacrylate esters.

7. The nonwoven fabric according to claim 1 bonded with the copolymer emulsion binder in which the hydroxyl-containing monomer is selected from the group consisting of hydroxyethyl acrylate, hydroxypropyl acrylate, hydroxyethyl methacrylate and hydroxypropyl methacrylate.

8. A process for preparing a nonwoven fabric from a loosely assembled mat of fibers comprising the steps of:
    (A) providing a loosely assembled mat of fibers;
    (B) providing a copolymer emulsion binder according to claim 1;
    (C) adding to the copolymer emulsion binder of step (B) a suitable catalyst to crosslink the emulsion binder to itself and to the fibers;
    (D) impregnating the fibers with the copolymer emulsion binder containing catalyst;
    (E) removing the excess binder; and
    (F) drying and curing the mat of fibers to effect bonding of the copolymer emulsion binder to the mat of fibers.

9. The process according to claim 8 in which the crosslinking catalyst of step (C) is selected from the group consisting of hydrochloric acid, oxalic acid, citric acid, and ammonium chloride.

* * * * *